US009389121B2

(12) United States Patent
Ross et al.

(10) Patent No.: US 9,389,121 B2
(45) Date of Patent: Jul. 12, 2016

(54) LINE LIGHT SOURCE FOR RAMAN OR OTHER SPECTROSCOPIC SYSTEM

(75) Inventors: Bradley B. Ross, Westerville, OH (US); Andrew P. Bartko, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 109 days.

(21) Appl. No.: 13/983,616

(22) PCT Filed: Feb. 8, 2012

(86) PCT No.: PCT/US2012/024239
§ 371 (c)(1),
(2), (4) Date: Sep. 20, 2013

(87) PCT Pub. No.: WO2012/109301
PCT Pub. Date: Aug. 16, 2012

(65) Prior Publication Data
US 2014/0002817 A1    Jan. 2, 2014

Related U.S. Application Data

(60) Provisional application No. 61/440,561, filed on Feb. 8, 2011.

(51) Int. Cl.
*G01J 3/44*    (2006.01)
*G01N 21/55*    (2014.01)
(Continued)

(52) U.S. Cl.
CPC .... *G01J 3/44* (2013.01); *G01J 3/10* (2013.01); *G01J 3/18* (2013.01); *G01J 3/28* (2013.01);
(Continued)

(58) Field of Classification Search
CPC .............. G01J 3/44–3/4412; G01J 2003/4418; G01J 2003/4424
See application file for complete search history.

(56) References Cited

U.S. PATENT DOCUMENTS 6,195,208 B1 *  2/2001  Ngoi ...................... G02B 27/09
                                                               359/641
7,339,148 B2    3/2008  Kawano et al.
(Continued)

FOREIGN PATENT DOCUMENTS

WO    WO 2007/009119 A2    1/2007
WO    WO 2008/117518 A1    10/2008

OTHER PUBLICATIONS

International Search Report and Written Opinion mailed Jun. 8, 2012.

*Primary Examiner* — Kara E Geisel
*Assistant Examiner* — Shawn Decenzo
(74) *Attorney, Agent, or Firm* — Richard M. Klein; Fay Sharpe LLP

(57) ABSTRACT

An apparatus comprises: a microscope objective focused on a microscope field of view; a light source including a laser generating an astigmatic beam and optics configured to couple the astigmatic beam into the microscope objective to produce high aspect ratio illumination at the microscope field of view; and a data acquisition system configured to generate data pertaining to light emanating from the microscope field of view responsive to the high aspect ratio illumination. The apparatus may be a Raman spectroscopy system. The laser may be an edge emitting laser. The optics of the light source may include an aspherical lens arranged to compensate the astigmatism of the astigmatic beam. The optics of the light source may include a diffraction grating arranged respective to the laser to provide feedback reducing a spectral full width at half maximum (FWHM) of the astigmatic beam.

20 Claims, 1 Drawing Sheet

(51) Int. Cl.
| | |
|---|---|
| *G01N 21/59* | (2006.01) |
| *G01N 21/64* | (2006.01) |
| *G01N 21/65* | (2006.01) |
| *G01J 3/28* | (2006.01) |
| *G02B 21/00* | (2006.01) |
| *G01J 3/10* | (2006.01) |
| *G01J 3/18* | (2006.01) |

(52) U.S. Cl.
CPC ............... *G01N 21/55* (2013.01); *G01N 21/59* (2013.01); *G01N 21/6458* (2013.01); *G01N 21/65* (2013.01); *G02B 21/0032* (2013.01); *G01N 2021/6417* (2013.01)

(56) References Cited

U.S. PATENT DOCUMENTS

| | | | |
|---|---|---|---|
| 7,791,013 B2* | 9/2010 | Wang et al. | 250/222.1 |
| RE42,251 E * | 3/2011 | Plut | 353/31 |
| 8,525,988 B2* | 9/2013 | Schoenfelder et al. | 356/326 |
| 2006/0176478 A1* | 8/2006 | Clarke et al. | 356/301 |
| 2008/0169752 A1 | 7/2008 | Hattori et al. | |
| 2010/0291599 A1 | 11/2010 | Tague, Jr. et al. | |

\* cited by examiner

LINE LIGHT SOURCE FOR RAMAN OR OTHER SPECTROSCOPIC SYSTEM

This application is a national stage entry of PCT/US2012/024239 filed Feb. 8, 2012 which claims the benefit of U.S. Provisional Application No. 61/440,561 filed Feb. 8, 2011 titled LINE LIGHT SOURCE FOR RAMAN OR OTHER SPECTROSCOPIC SYSTEM and naming inventors Bradley B. Ross and Andrew P. Bartko. U.S. Provisional Application No. 61/440,561 filed Feb. 8, 2011 is incorporated herein by reference in its entirety.

BACKGROUND

The following relates to the spectroscopy arts, Raman spectroscopy arts, particulate detection or sampling arts, optical characterization arts, and so forth.

WO 2007/009119 A2 published Jan. 18, 2007 is incorporated herein by reference in its entirety. WO 2007/009119 A2 relates to systems and methods for biological and chemical detection and names Battelle Memorial Institute, Columbus, Ohio, USA as applicant.

Raman spectroscopy is known for use in microbiological testing. By way of illustrative example, some such techniques are disclosed in WO 2007/009119 A2, and a known microbiological testing system employing Raman spectroscopy is the Resource Effective Bioidentification System (REBS) developed by Battelle Memorial Laboratories (Columbus, Ohio, USA).

In some types of microscopy, line illumination is employed. Such illumination advantageously provides high resolution controlled by the "width" or narrow dimension of the line illumination, and parallel sampling along the "length" or long dimension of the line. For some cell detection or sampling (e.g., counting) applications, the width of the line illumination is preferably about one micron, which corresponds to a typical size of prokaryotic cells (bacteria, by way of illustrative example) of interest in medical, biohazard, or other applications.

Typical light sources for illuminating the microscope field of view include arc lamps and semiconductor lasers. Such light sources are commercially available, but are generally designed to produce circular illumination. In the case of edge emitting diode lasers, which naturally produce a high aspect ratio beam, the commercial product is typically packaged with micro-optical components (a micro-cylindrical lens, by way of illustrative example) to circularize the beam output. The circular beam is converted to line illumination of the desired aspect ratio using an aspherical lens, cylindrical lens, or the like.

In the context of sampling microarrays, it has also been suggested to produce line illumination by focusing the high aspect ratio beam of an edge emitting diode laser. See WO 2008/0117518 A1. However, an edge emitting laser actually generates a strongly diverging beam with a high degree of astigmatism. In commercially available edge emitting laser packages, a microlens or other near-field optic is typically provided to circularize the output beam. Moreover, Raman spectroscopy and some other spectroscopy techniques require a highly monochromatic light source. For example, in the case of Raman a spectral full width at half maximum (FWHM) of order 0.1 nanometers or smaller is desired. An edge emitting laser produces a beam with a large spectral FWHM, for example, of order 3 nanometers in the case of some commercially available edge emitting lasers.

BRIEF SUMMARY

In accordance with certain aspects disclosed herein, an apparatus comprises: a microscope objective focused on a microscope field of view; a light source including a laser generating an astigmatic beam and optics configured to couple the astigmatic beam into the microscope objective to produce high aspect ratio illumination at the microscope field of view; and a data acquisition system configured to generate data pertaining to light emanating from the microscope field of view responsive to the high aspect ratio illumination. In some embodiments the laser is an edge emitting laser and the astigmatic beam generated by the edge emitting laser has astigmatism $\tan(\beta)/\tan(\alpha)$ of at least forty where $\beta$ is the beam divergence angle transverse to the emission plane of the edge emitting laser and $\alpha$ is the beam divergence angle in the emission plane of the edge emitting laser. In some embodiments the optics of the light source comprise an aspherical lens arranged to compensate the astigmatism of the astigmatic beam. In some embodiments the optics of the light source comprise a diffraction grating arranged respective to the laser to provide feedback reducing a spectral full width at half maximum (FWHM) of the astigmatic beam.

In accordance with certain aspects disclosed herein, an apparatus comprises: a laser generating an astigmatic beam; an aspherical lens arranged to convert the astigmatic beam into an astigmatism corrected beam; and a microscope objective focused on a microscope field of view that receives the astigmatism corrected beam and produces high aspect ratio illumination at the microscope field of view. In some embodiments the laser is an edge emitting laser. In some embodiments employing an edge emitting laser, a diffraction grating is arranged respective to the edge emitting laser to provide feedback reducing a spectral full width at half maximum (FWHM) of the astigmatic beam.

In accordance with certain aspects disclosed herein, a Raman spectroscopy system is disclosed which employs an apparatus as set forth in the immediately preceding paragraph.

In accordance with certain aspects disclosed herein, a method comprises: generating an astigmatic beam; correcting astigmatism of the astigmatic beam to produce an astigmatism corrected beam; using a microscope objective to produce high aspect ratio illumination at a microscope field of view from the astigmatism-corrected beam; and generating data pertaining to light emanating from the microscope field of view responsive to the high aspect ratio illumination. In some embodiments the generating comprises generating data pertaining to Raman scattering of the high aspect ratio illumination.

BRIEF DESCRIPTION OF THE DRAWINGS

The invention may take form in various components and arrangements of components, and in various process operations and arrangements of process operations. The drawings are only for purposes of illustrating preferred embodiments and are not to be construed as limiting the invention.

DETAILED DESCRIPTION OF PREFERRED EMBODIMENTS

Figure 1:
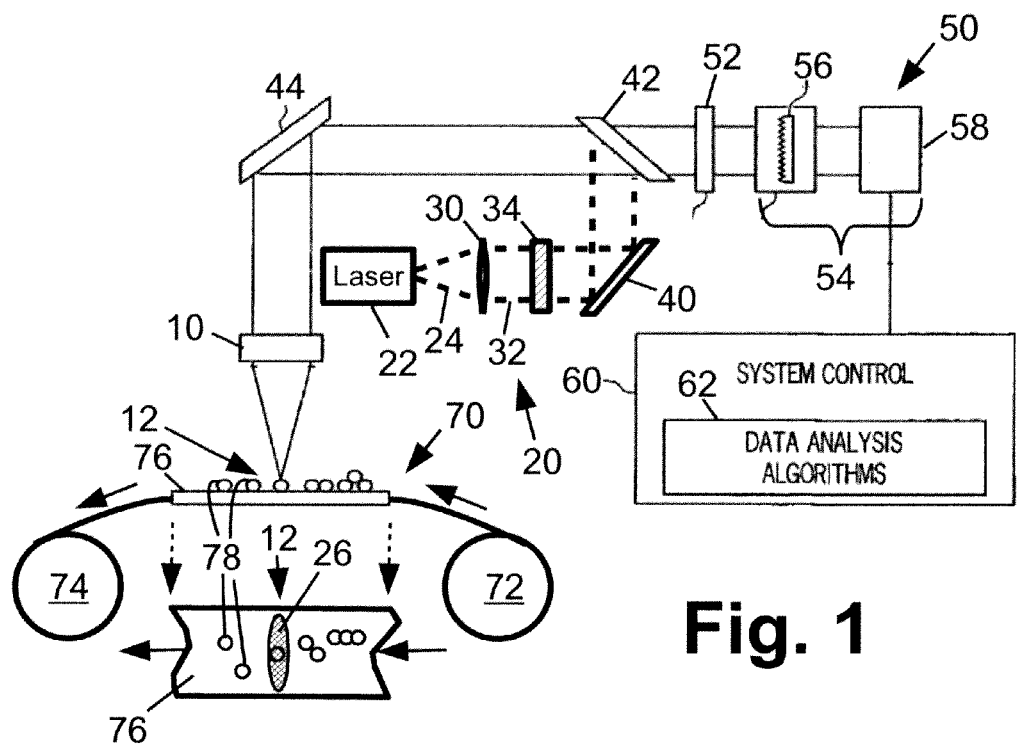
FIG. 1 diagrammatically shows a Raman spectroscopy system.
Figure 2:
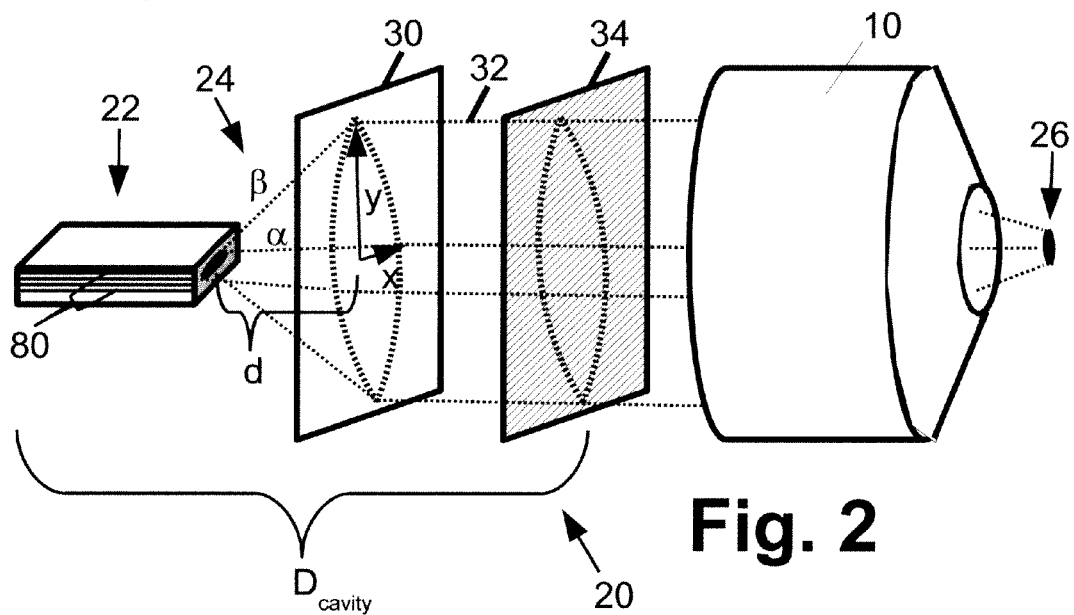
FIG. 2 diagrammatically shows a perspective view of the light source of the Raman spectroscopy system of FIG. 1.

With reference to FIGS. 1 and 2, an illustrative Raman spectroscopy system includes a microscope objective 10 focused on a microscope field of view 12, a light source 20 including a laser 22 generating an astigmatic beam 24 and optics configured to couple the astigmatic beam 24 into the microscope objective 10 to produce high aspect ratio illumination 26 at the microscope field of view 12. In FIG. 1, the microscope field of view 12 is shown "on-edge" in the main figure, and an inset indicated by dashed arrows shows a plan-view of the microscope field of view 12 including a diagrammatic depiction of the high aspect ratio illumination 26. The optics of the illustrative light source 20 include an aspherical lens 30 arranged to compensate the astigmatism of the astigmatic beam 24 to form an astigmatism-corrected beam 32. The illustrative optics also include a diffraction grating 34 arranged respective to the laser 22 to provide feedback reducing a spectral full width at half maximum (FWHM) of the astigmatic beam 24. It will be appreciated that reducing the spectral FWHM of the astigmatic beam 24 inherently also reduces the spectral FWHM of the astigmatism-corrected beam 32 and of the high aspect ratio illumination 26.

In the illustrative example of FIG. 1, additional mirrors 40, 42, 44 (which may optionally be dichotic or partially reflective mirrors) are included to direct the astigmatism-corrected beam 32 into the microscope objective 10. It will be appreciated that these mirrors 40, 42 are optional and may be omitted or replaced or supplemented by other optics, e.g. other or additional mirrors, beam-steering lenses or gratings or so forth. The illustrative mirror 42 is a partially reflective mirror that permits light emanating from the microscope field of view 12 responsive to the high aspect ratio illumination 26 to be captured using the microscope objective 10 and directed to a data acquisition system 50. Alternatively, separate illumination and acquisition (or collection) microscope objectives may be employed. Additional optical components may be included in the optics of the light source, such as polarizers, beam width-modifying lens sets, neutral density filters, diverters for redirecting a portion of the beam to an intensity meter for monitoring purposes, or so forth. FIG. 2 shows a simplified version of the light source 20 coupled with the microscope objective 10 in which the mirrors 40, 42, 44 are omitted.

The data acquisition system 50 is configured to generate data pertaining to light emanating from the microscope field of view 12 responsive to the high aspect ratio illumination 26. The illustrative example of FIG. 1 is a Raman spectroscopy system designed to detect particles 52 dispersed on the microscope field of view 12. The illustrative Raman data acquisition system 50 includes optional optics 52 (for example, filtering to remove wavelength components unrelated to Raman scattering), followed by a spectrometer 54 including a light-dispersive element 56 and an optical detector 58 (which in some embodiments may be an array of light detectors 58). In some embodiments, the light-dispersive element is coupled with an array of light detectors with the light detector elements arranged to detect different portions (i.e., wavelengths or wavelength bins) of the dispersed light. In other embodiments, the light dispersive element rotates or moves relative to a fixed light detector, for example as in a Czerny-Turner monochromator in which a diffraction grating is tilted such that different wavelengths pass through a light output slit to be detected by the light detector. Alternatively, the light dispersive element may be fixed and the light detector may move. Other embodiments are also contemplated for the spectrometer 54, such as being embodied as a Fourier Transform Infrared Spectrometer (FTIR).

The output of the spectrometer 54 (or more particularly the light detector or light detector array 58) is an electrical signal that is input to a system control unit 60 which is suitably embodied as a digital processor (e.g., a computer, a network server, a graphical processing unit or GPU, a dedicated digital processing device, or so forth) executing suitable data analysis algorithms 62. In the illustrative Raman spectroscopy example, the system control unit 60 generates Raman scattering data from the output of the spectrometer 54, and in some embodiments includes a display and/or printing device (not shown) for displaying or printing a Raman spectrum.

The Raman spectroscopy system of FIG. 1 is an illustrative spectroscopy application of the light source 20. Other spectroscopy systems can also employ the light source 20, such as a reflected light spectroscopy system (for example, to measure a reflectance spectrum of a material at the microscope field of view, (ii) a transmitted light spectroscopy system (for example, to measure transmittance through a material at the microscope field of view), a fluorescence spectroscopy system configured to measure fluorescence excited by the high aspect ratio illumination, and the illustrative Raman spectroscopy system that measures high aspect ratio illumination scattered by Raman scattering at the microscope field of view. WO 2007/009119 A2, which published Jan. 18, 2007 is incorporated herein by reference in its entirety, discloses additional Raman spectroscopy embodiments and aspects, as well as embodiments of other types of spectroscopy systems including various combinations of different types of spectroscopy systems.

The illustrative Raman spectroscopy system of FIG. 1 is suitably used for biological and chemical detection. In the illustrative example, a sample stage is embodied as a roll-to-roll apparatus 70 including a source roll 72 and a take-up roll 74 that moves a surface 76 across the microscope field of view 12. Particles 78 disposed on the surface 76 are detected based on a characteristic Raman scattering signal generated by the particle 78 responsive to the high aspect ratio illumination 26. In other embodiments, the particles may emit a characteristic fluorescence signal that is detected by a fluorescence spectroscopy system. In this regard, it should be noted that the term "spectroscopy system" as used herein does not require collection of a spectrum over a contiguous spectral range—rather, by way of illustrative example, the spectroscopy system may monitor one or more Raman scattering wavelengths (or fluorescence wavelengths in a fluorescence spectroscopy embodiment) that are characteristic of the particles 78. The type and nature of the particles 78 is specific to the application. For some medical applications, the particles 78 may be bacteria cells or other prokaryotic cells. In rare cell detection applications, the particles 78 may be a certain type of epithelial cells that are indicative of a certain type of cancer. As yet another example, the particles 78 may be particles of a certain hazardous material or chemical that is to be detected.

For particle detection, it is advantageous for the moving sample surface and the high aspect ratio illumination 26 at the microscope field of view 12 to be relatively oriented as shown in FIG. 1, that is, with the sample surface 76 moving across the microscope field of view 12 in a direction transverse to the long side of the high aspect illumination 26 at the microscope field of view 12. In this relative orientation, it is further advantageous from a sampling resolution standpoint for the short side of the high aspect illumination 26 at the microscope field of view 12 to be commensurate with the average size of the particles 78 to be detected. In the case of bacteria or other prokaryotic cells, this dimension is about one micron, and so it is advantageous for the short side of the high aspect illumination 26 at the microscope field of view 12 to have a dimension of 1-3 micron inclusive in some embodiments. The dimension of the long side of the high aspect illumination 26 at the microscope field of view 12 affects the sampling speed (a longer side samples more area per unit time movement of the surface 76); however, the long side should not be so long as to be statistically likely to sample two or more of the particles 78 at the same time. In some embodiments the long side has a dimension of at least 30 microns. In some embodiments the long side has a dimension of at least 40 microns. In some embodiments the long side has a dimension of at least 50 microns. These are merely illustrative examples, and the dimensions of the high aspect illumination 26 at the microscope field of view 12 are suitably determined on an application-specific basis taking into account factors such as the average size of the particles to be detected and the density of such particles on the sample surface.

WO 2007/009119 A2, which published Jan. 18, 2007 and is incorporated herein by reference in its entirety, discloses additional embodiments and aspects of biological and chemical detection, employing Raman spectroscopy, fluorescence, or so forth. Moreover, particle detection is to be understood to be merely an illustrative application; more generally, the light source 20 may be employed in other applications of spectroscopy.

With particular reference to FIG. 2, further aspects of the light source 20 are described. The laser 22 which generates the astigmatic beam 24 is, in the illustrative example, an edge emitting laser, such as a semiconductor-based edge emitting diode laser. A semiconductor-based edge emitting laser includes a stack of semiconductor layers 80, one or more of which define an active layer in which light amplification by stimulated emission of radiation (that is, lasing or laser action) takes place. By way of illustrative example, the stack of semiconductor layers 80 may be a stack of epitaxial group III-V compound semiconductor layers. Such a stack of epitaxial group III-V compound semiconductor layers may include a binary, ternary, or quaternary group III-V compound semiconductor active layer including at least one group III species selected from the group consisting of Ga, Al, and In and including at least one group V species selected from the group consisting of As, P, N, and Sb.

To form a laser cavity, a resonant cavity containing at least the active layer, and possibly including additional optical cladding layers, is defined by optically reflective layers of the stack of semiconductor layers 80 and/or by metallic coatings or layers or other non-semiconductor reflective layers parallel with the layers of the stack of semiconductor layers 80. The result is that the resonant cavity of the edge emitting laser 22 has a high aspect ratio, that is, is essentially an emission "plane".

As labeled in FIG. 2, the astigmatic beam 24 has a largest beam divergence angle $\beta$ transverse to the emission plane of the edge emitting laser 22, and has a smallest beam divergence angle $\alpha$ in the emission plane of the edge emitting laser. (More generally, the astigmatic beam 24 inherently has a divergence angle that varies with angle around the beam, and hence inherently has a largest beam divergence angle $\beta$ and a smallest beam divergence angle $\alpha$ where $\beta>\alpha$). The astigmatic beam 24 has a cross section in the far field (denoted by a distance d in FIG. 2) with a high aspect ratio y:x where $y=d \times \tan(\beta)$ and $x=d \times \tan(\alpha)$. (This far-field estimate neglects the small but finite dimensions of the actual emission plane of the edge emitting laser 22). Thus, the astigmatic beam 24 has a cross section in the far field with an aspect ratio of $\tan(\beta):\tan(\alpha)$. It will be noted that this aspect ratio is independent of the distance d into the far field.

With continuing reference to FIG. 2, the aspherical lens 30 is arranged to compensate the astigmatism of the astigmatic beam 24 to form the astigmatism-corrected beam 32. It will be noticed that the aspect ratio $\tan(\beta):\tan(\alpha)$ of the cross-section of the astigmatic beam 24 in the far field is independent of the distance d into the far field. Accordingly, the aspherical lens 30 can be placed at any distance in the far field from the edge emitting laser 22. By way of illustrative example, the aspherical lens 30 is located at the distance d in FIG. 2. Moreover, it should be noted that the aspherical lens 30 does not have to be located "in the far field"—a closer placement of the aspherical lens 30 to the laser 22 merely distorts the cross-section aspect ratio slightly due to effects of the finite emission "plane" of the edge emitting laser 22.

The aspherical lens 30 has different foci in the orthogonal directions, i.e. in the "x" and "y" directions as denoted in FIG. 2. The foci of the aspherical lens 30 are chosen and aligned respective to the astigmatism of the astigmatic beam 22 so as to compensate the astigmatism of the astigmatic beam 24 to form the astigmatism-corrected beam 32. Thus, the focal length of the aspherical lens 30 for the "y" direction should be chosen to collimate light with the largest beam divergence $\beta$, while the focal length of the aspherical lens 30 for the "x" direction should be chosen to collimate light with the smallest beam divergence $\alpha$. In some embodiments, the smallest beam divergence $\alpha$ is sufficiently small to be considered negligible—in such embodiments, the focal length of the aspherical lens 30 for the "x" direction is suitably chosen to be infinite, and the aspherical lens 30 is suitably embodied as a cylindrical lens having no curvature along the "x" direction.

The astigmatism-corrected beam 32 is collimated and has a large aspect ratio of $\tan(\beta):\tan(\alpha)$. This astigmatism-corrected beam 32 is imaged by the microscope objective 10 to form the high aspect ratio illumination 26 at the microscope field of view 12 also having the large aspect ratio of $\tan(\beta):\tan(\alpha)$.

In some embodiments, the high aspect ratio illumination 26 at the microscope field of view 12 is chosen to have a short dimension of about 1 micron as is suitable for detection of bacteria or other prokaryotic cells. Advantageously, the beam emitted by the laser 22 is typically of this order of magnitude in size—accordingly, the magnification of the overall optical system including the aspherical lens 30 and the microscope objective 10 is about unity. Since large magnification or demagnification is not involved, errors or distortions due to lens aberrations or other optical system imperfections are advantageously reduced.

In the light source 20 of FIG. 2, the edge emitting laser 22 does not include a microlens or other near field optic for circularizing the astigmatic beam, as is conventionally included in commercial edge emitting laser packages. Rather the light source 20 of FIG. 2 employs the laser 22 without such circularizing optics, so that the astigmatic beam 24 is output with a high degree of astigmatism (e.g., $\tan(\beta):\tan(\alpha)$ of 50 or higher in some contemplated embodiments). Instead of attempting to circularize the beam, the light source 20 takes advantage of the combination of high astigmatism and large divergence (at least in the "y" direction) of to automatically generate a beam with a cross-section that is both (i) relatively large (the precise size being determined by the distance d in FIG. 2) and (ii) having a large aspect ratio. The aspherical lens 30 then operates to compensate the astigmatism, but not the high aspect ratio, so as to provide the astigmatism-corrected beam 32 which does not have astigmatism but which does have a large aspect ratio commensurate with the astigmatism—the aspect ratio is about $\tan(\beta):\tan(\alpha)$. Because the astigmatism is not corrected in the near field, the aspherical lens 30 is not a micro-optical component and consequently its manufacturing is simplified.

With continuing reference to FIG. 2, some spectroscopy applications call for the spectral full width at half maximum (FWHM) of the light source to be small. For example, in Raman spectroscopy the spectral FWHM of the light source is preferably less than 0.1 nanometer, and in some embodiments is preferably about 0.05 nanometer or smaller. Semiconductor lasers, however, tend to generate beams with spectral FWHM substantially larger than this. For example, a typical spectral FWHM for a semiconductor-based edge emitting diode laser is about 3 nanometers. In some embodiments, the optics of the light source include a laser line filter having a narrow spectral pass-band meeting the stringent spectroscopy requirement. However, this approach discards a large portion of the spectrum (and hence discards a large portion of the intensity) of the astigmatic beam.

In the illustrated embodiment, spectral FWHM narrowing is achieved by using the diffraction grating 34 arranged respective to the laser 22 to provide feedback reducing a spectral full width at half maximum (FWHM) of the astigmatic beam 24. As previously noted, this inherently also reduces the spectral FWHM of the astigmatism-corrected beam 32 and of the high aspect ratio illumination 26. In effect, the diffraction grating 34 creates an extended resonant cavity of length $D_{cavity}$ as labeled in FIG. 2. The resonance condition for the astigmatic beam 24 includes resonance in the internal resonant cavity of the laser 22, and also includes resonance over the resonant cavity of length $D_{cavity}$ defined by the relative separation between the laser 22 and diffraction grating 34.

Substantially any diffraction grating can be employed. In some embodiments the diffraction grating 34 is embodied as a volume phase grating, such as (by way of illustrative example) a volume phase holography diffraction gating. Although in illustrative FIG. 2 the diffraction grating 34 is located after the aspherical lens 30 in the optical train, it is also contemplated to place the diffraction grating between the laser and the aspherical lens. Moreover, if the spectral FWHM of the laser 22 operating without the diffraction grating 34 is adequate for the specific spectroscopy application, then the diffraction grating 34 is optionally omitted entirely.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

The invention claimed is:

1. An apparatus comprising:
    a microscope objective focused on a microscope field of view;
    a light source including a laser generating an astigmatic beam having astigmatism $\tan(\beta)/\tan(\alpha)$ where $\beta$ is the largest beam divergence angle of the astigmatic beam and $\alpha$ is the smallest beam divergence angle of the astigmatic beam; and
    optics configured to couple the astigmatic beam into the microscope objective to produce high aspect ratio illumination at the microscope field of view wherein the optics comprise an aspherical lens arranged to compensate the astigmatism of the astigmatic beam wherein the aspherical lens has a finite focal length in the direction of the largest beam divergence angle $\beta$ effective to collimate light with the largest beam divergence angle $\beta$ and has a finite focal length in the direction of the smallest beam divergence angle $\alpha$ effective to collimate light with the smallest beam divergence angle $\alpha$ to convert the astigmatic beam to a collimated beam and the microscope objective images the collimated beam at the microscope field of view to produce the high aspect ratio illumination at the microscope field of view; and
    a data acquisition system configured to generate data pertaining to light emanating from the microscope field of view responsive to the high aspect ratio illumination.

2. The apparatus as set forth in claim 1, wherein the laser comprises an edge emitting laser.

3. The apparatus as set forth in claim 1, wherein the data acquisition system comprises:
    a spectrometer configured to generate said data.

4. The apparatus as set forth in claim 3, wherein the spectrometer is configured to generate said data comprising a Raman spectrum.

5. The apparatus as set forth in claim 1, further comprising:
    a sample stage configured to move a surface across the microscope field of view in a direction transverse to the long side of the high aspect illumination at the microscope field of view;
    wherein the data acquisition system is configured to generate data pertaining to at least one of (i) reflected light, (ii) transmitted light, (iii) fluorescence excited by the high aspect ratio illumination, and (iv) high aspect ratio illumination scattered by Raman scattering at the microscope field of view.

6. The apparatus as set forth in claim 1, wherein the laser is an edge emitting laser and the astigmatic beam generated by the edge emitting laser has astigmatism $\tan(\beta)/\tan(\alpha)$ of at least forty.

7. The apparatus as set forth in claim 1, wherein the astigmatic beam generated by the laser has astigmatism $\tan(\beta)/\tan(\alpha)$ of at least forty.

8. The apparatus as set forth in claim 1, wherein the high aspect ratio illumination at the microscope field of view has an aspect ratio of at least 40:1.

9. The apparatus as set forth in claim 1, wherein:
    the high aspect ratio illumination at the microscope field of view has an aspect ratio of $\tan(\beta):\tan(\alpha)$.

10. The apparatus as set forth in claim 9, wherein $\tan(\beta)/\tan(\alpha)$ is greater than or equal to 30.

11. The apparatus as set forth in claim 1, wherein the optics of the light source comprise a diffraction grating arranged respective to the laser to provide feedback reducing a spectral full width at half maximum (FWHM) of the astigmatic beam.

12. The apparatus as set forth in claim 11, wherein:
    the laser is an edge emitting laser that, in the absence of the diffraction grating, would produce a beam having a spectral FWHM of at least one nanometer, and
    wherein in the presence of the diffraction grating the spectral FWHM of the astigmatic beam is reduced to less than 0.1 nanometer.

13. An apparatus comprising:
    a laser generating an astigmatic beam with largest beam divergence angle $\beta$ in a y-direction and smallest beam divergence angle $\alpha$ in an x-direction orthogonal to the y-direction;
    an aspherical lens arranged to collimate the astigmatic beam into a collimated astigmatism-corrected high aspect ratio beam having an aspect ratio of $\tan(\beta):\tan(\alpha)$ wherein the aspherical lens has a finite focal length in the y-direction effective to collimate light with the largest beam divergence angle $\beta$ and has a finite focal length in the x-direction effective to collimate light with the smallest beam divergence angle $\alpha$; and
    a microscope objective focused on a microscope field of view that receives and focuses the collimated astigmatism-corrected high aspect ratio beam at the microscope field of view to produce high aspect ratio illumination at the microscope field of view having an aspect ratio of $\tan(\beta):\tan(\alpha)$.

14. The apparatus of claim 13, wherein the laser is an edge emitting laser generating the astigmatic beam with the largest beam divergence angle β transverse to the emission plane of the edge emitting laser and the smallest beam divergence angle α in the emission plane of the edge emitting laser.

15. The apparatus of claim 14, further comprising:
a diffraction grating arranged respective to the edge emitting laser to provide feedback reducing a spectral full width at half maximum (FWHM) of the astigmatic beam.

16. The apparatus of claim 15, wherein the diffraction grating comprises a volume phase grating that reduces the spectral FWHM of the astigmatic beam by at least a factor of ten.

17. A method comprising:
generating an astigmatic beam with largest beam divergence angle β and smallest beam divergence angle α;
simultaneously collimating the astigmatic beam and correcting astigmatism of the astigmatic beam using an aspherical lens to produce an astigmatism-corrected collimated beam having an aspect ratio of tan(β):tan(α) wherein the aspherical lens has a finite focal length in the direction of the largest beam divergence effective to collimate light with the largest beam divergence angle β and a finite focal length in the direction of the smallest beam divergence effective to collimate light with the smallest beam divergence angle α;
using a microscope objective to produce high aspect ratio illumination at a microscope field of view by focusing the astigmatism-corrected beam at the microscope field of view to produce the high aspect ratio illumination at the microscope field of view having an aspect ratio of tan(β):tan(α); and
generating data pertaining to light emanating from the microscope field of view responsive to the high aspect ratio illumination.

18. The method of claim 17, wherein the generating comprises:
generating data pertaining to Raman scattering of the high aspect ratio illumination.

19. The method of claim 17, further comprising:
generating the astigmatic beam using an edge emitting laser.

20. The method of claim 19, further comprising:
providing feedback using a diffraction grating to reduce a spectral full width at half maximum (FWHM) of the astigmatic beam.

\* \* \* \* \*